(12) United States Patent
Hvalsøe et al.

(10) Patent No.: US 12,263,337 B2
(45) Date of Patent: Apr. 1, 2025

(54) SYSTEM FOR ELECTRICAL STIMULATION OF NERVES

(71) Applicant: INNOCON MEDICAL APS, Aalborg (DK)

(72) Inventors: Torsten Fjeldgaard Hvalsøe, Aalborg (DK); Dianna Marsk Knudsen, Løgstør (DK); Jesper Nielsen, Klarup (DK)

(73) Assignee: INNOCON MEDICAL APS, Aalborg (DK)

( * ) Notice: Subject to any disclaimer, the term of this patent is extended or adjusted under 35 U.S.C. 154(b) by 470 days.

(21) Appl. No.: 17/431,703

(22) PCT Filed: Feb. 17, 2020

(86) PCT No.: PCT/DK2020/050040
§ 371 (c)(1),
(2) Date: Aug. 17, 2021

(87) PCT Pub. No.: WO2020/164678
PCT Pub. Date: Aug. 20, 2020

(65) Prior Publication Data
US 2022/0118245 A1    Apr. 21, 2022

(30) Foreign Application Priority Data
Feb. 17, 2019    (DK) ............................ PA201900211

(51) Int. Cl.
*A61N 1/05*    (2006.01)
*A61N 1/04*    (2006.01)

(52) U.S. Cl.
CPC ......... *A61N 1/0521* (2013.01); *A61N 1/0456* (2013.01); *A61N 1/0496* (2013.01); *A61N 1/0502* (2013.01)

(58) Field of Classification Search
None
See application file for complete search history.

(56) References Cited

U.S. PATENT DOCUMENTS

| 5,144,952 A * | 9/1992 | Frachet ................... A61N 1/05 607/57 |
| 6,865,907 B2 * | 3/2005 | Andrews ............ A44C 15/0035 63/12 |
| 9,101,277 B2 * | 8/2015 | Doerr ................... A61N 1/0502 |
| 9,364,667 B1 | 6/2016 | Dinsmoor |
| 2015/0201719 A1 * | 7/2015 | Seely ................... A44C 7/002 63/12 |

FOREIGN PATENT DOCUMENTS

| WO | 2012019034 A1 | 2/2012 |
| WO | 2019034223 A1 | 2/2019 |

OTHER PUBLICATIONS

Written Opinion of the International Searching Authority issued in PCT/DK2020/050040, dated May 12, 2020, 4 pgs.
International Search Report issued in PCT/DK2020/050040, dated May 12, 2020, 2 pgs.

* cited by examiner

*Primary Examiner* — Michael W Kahelin
(74) *Attorney, Agent, or Firm* — HOLLAND & HART LLP

(57) ABSTRACT

In a system for electrical stimulation of nerves of a living being a pulse generator is configured to provide a sequence of electrical and/or vibration pulses to at least one electrode and/or vibration generator that are maintained in close proximity to the nerve of interest with the use of means for securing the electrode to the skin or tissue of the living being.

13 Claims, 3 Drawing Sheets

SYSTEM FOR ELECTRICAL STIMULATION OF NERVES

CROSS-REFERENCE TO RELATED APPLICATIONS

This is a national phase application of International Application No. PCT/DK2020/050040, filed 17 Feb. 2020, which claims the benefit of Danish Patent Application No. PA201900211, filed 17 Feb. 2019, the disclosures of which are incorporated, in their entireties, by this reference.

TECHNICAL FIELD

The present invention is generally concerned with stimulation of nerves.

BACKGROUND OF THE INVENTION

Stimulation of nerves is known to have a positive effect on a variety of illnesses that derives from a defective nervous system. Electrical stimulation of the vagus nerve has as an example proven to be an efficacious treatment of epilepsy. It has also been shown that stimulation of the genital nerves can have a positive effect in the treatment of fecal and urinary incontinence. Tactile or mechanical stimulation is a natural means of stimulation, and it has previously been shown that one can stimulate the nerves of the pelvic floor by means of transcutaneous mechanical nerve stimulation (TMNS) done through vibration.

For the sake of explaining the invention, the treatment of incontinence has been chosen to exemplify the advantageous features but should not be taken as limiting for the scope of the invention for which the inventive concept could be carried out in order to stimulate nerves contained in the human body without specifying the reason for stimulating the specific nerve.

Overactive bladder (OAB) syndrome is a highly prevalent condition worldwide, particularly in the general population above 40 years, where prevalence has been reported to be about 17%. Frequency (85%) is the most commonly reported symptom, followed by urgency (54%) and urge urinary incontinence (36%). These symptoms adversely affect patients' quality of life due to social and hygienic difficulties. Upper urinary tract damage caused by sustained high intravesical pressures and repeated bladder infections is another concern that causes morbidity, hospitalization or even death. Conventional treatment is typically based on drugs with dose-limiting systemic side effects.

Fecal incontinence (FI) is also highly frequent with prevalence between 5-15% in the general population. It is commonly defined as the involuntary loss of solid or liquid feces or mucus and is a disabling symptom, which can have a devastating impact on quality of life, as its effects may include embarrassment, social isolation, and even loss of employment. Conservative treatment may be dietetic measures, various pharmacological agents, anorectal rehabilitation, and transanal irrigation.

In both OAB and FI surgical destructive interventions may be considered if patients are refractory to conventional treatment options but complication rates are often high. Alternative treatment options should be considered in refractory patients to avoid destructive surgery.

Continuous or intermittent electrical stimulation of the sacral nerves is known to be effective in the treatment of a variety of pelvic disorders, such as OAB and FI (InterStim® Therapy, Medtronic, MN, USA). InterStim® Therapy is based on electrical stimulation of the sacral root/s using a medical lead connected to an implanted pulse generator. Electrical stimulation of the sacral root/s activates sacral somatic afferents that modulate the sacral reflex pathways. This effect is also known as neuromodulation and has been shown to reduce the symptoms of OAB and FI.

However, a completely implantable system is quite expensive in both hardware costs and for the act of implanting the whole system into the living being. Additionally, implanting a medical system into a living being should only be offered if alternative solutions available have failed. There seems to be a need for a simpler and affordable solution that provides an acceptable therapy to the outlined problem without the need for fully implantable systems.

US 2015/0352357 A1 to Medtronic present a solution providing a surface electrode in two variants. One for male use and one for female use, each variant designed with attempt to take advantage of the specific shape of the genitals of the genders and attempting to arrange electrodes that target the genital nerves. However, the disclosure does not explain how the electrodes are arranged and secured in a desired position where an effective electrical charge can be addressed towards the genital nerves.

Typically, surface electrodes are patch-type electrodes utilizing an adhesive and conductive hydrogel, with various supportive scrims and fabrics for strength and structural support. Due to the necessity of supportive scrims and wire meshes most types of such electrodes becomes relatively stiff and rigid. This has the effect that the electrodes looseness from the skin to which they are applied, especially during activity, or when applied to uneven structures or moistened skin such as on the genitals or at the Achilles tendon, leading to loss of functionality.

Thus, there is a need for an improvement that provides a stable electrode interface towards the genital nerves and provides a secure arrangement through the skin of the human being at the position of interest in close proximity to the genital nerves.

DESCRIPTION OF THE INVENTION

It is an object of the embodiments of the present invention to provide a system, which overcomes or at least reduces the above-mentioned disadvantages.

The present invention provides a solution, where the electrode/s and/or vibration generator/s is secured by the adhesive properties of the functional hydrogel formulations so that it is kept in constant distance and with constant orientation with regard to the position of the part of the nerve and/or its branches intended to be treated, thus the electrode/s and/or a vibration generator/s and the nerve being positioned mutually in the same stable position with regard to each other, even during exercise.

The invention discloses a stimulation media fixation unit which when exclusively providing electrical stimulation constitutes an electrode fixation unit, and when exclusively providing mechanical stimulation constitutes a vibration generator fixation unit. The invention further includes variants of the stimulation media fixation unit where electrical and/or mechanical stimulation can be provided simultaneously. In the event an electrode is present as part of the stimulation media fixation unit, then it is comprehended as an electrode fixation unit even though it also features a vibrations generator.

A ground, anode/return electrode may be positioned in close proximity of the cathode electrode/stimulating electrode, or distant, eventually as a patch type/skin electrode.

The latter may provide an option for a relative larger electrode attached to or integrated into the stimulation media fixation unit, thus eliminating many of the concerns to be addressed for the cathode electrode, including being positioned on less challenging parts of the body, and providing options for freedom of positioning at convenience of the user. However, some male users may have body hair covering most of the abdomen and may therefore prefer bipolar designs rather than larger return patch type electrodes. Daily handling of a bipolar electrode is considered advantageous, as the patch type electrode is then fully discarded. Therefore, the bipolar configuration is considered a superior design in most use-cases.

The application may require either quick-onset of the stimulation if/when requested, continuous stimulation during day and/or night, including periodic therapy sessions, depending of the clinically supported setup for the specific patient/user. Thus, the reliability of the fixation is of crucial importance for the product and may be a different use scenario compared to many available applications.

An important aspect is the freedom of movement appreciated during everyday activities such as walking, biking, running or other sports related activities, even further stressing out the critical importance of reliable and comfortable fixation of electrode/s. By further providing the options of mechanical vibrations stimulation or combining electrical stimulation with mechanical vibration, additional individual means of setup are thus available to the user's preference/s, and options for selection of specific treatments for the health care provider.

More specifically, fixation of neuromodulation electrodes for methods to treat pelvic floor disorders, such as urinary and fecal incontinence, by stimulation of the left and/or right branches of the dorsal genital nerves, or pudendal nerve afferents, is according to the present invention implemented using a stimulation media fixation unit inserted through the cutaneous tissue in the region along the penis, and/or at or near the glans of the clitoris, in close proximity of the targeted nerve/s, to support the arrangement of neuromodulation electrodes. Additionally, mechanical vibration as a supportive or alternative means is provided, by built-in vibration generator/s in electrode member/s of the stimulation media fixation units.

The intended level of fixation shall prevent the electrodes or means for mechanical vibration from dislocating from the site in the tissue intended to be stimulated.

In males the dorsal genital nerve is superficial on the dorsal side (i.e. at approximately the upper ¼ of the cross section of the penis) and runs along the length of the shaft of the penis until it reaches the glans, where it fans out.

In females the dorsal genital nerves tend to be close to the mucous membrane (or skin) near the glans of the clitoris between the labium minus and labium majus. Thus, these sites of stimulation are effective for both males and females, since factors such as fat layer and muscle tissue have a significant influence on the activation of the targeted nerves. At the intended site of stimulation, the fat layer is limited, and no muscles cover the nerves.

A reliable means of fixation in the tissue is presented by use of a stimulation media fixation unit, which is arranged in a formed channel in and out of the skin at the targeted tissue to be stimulated. In general, the disclosure is directed to fixation means of piercing the skin to fixate electrical stimulating electrode/s and mechanical vibration micromotor/s for delivering of electrical, vibrations or combinations of electrical and vibrations stimulation.

The invention is explained using a variant of the inventive electrode system, capable of holding vibration micro-motor/s, for treating incontinence, but it has to be understood that the concept can be used on the entire body where access to nerves underlying the skin is targeted electrical and/or mechanical stimulation. It could be on the neck for electrically treating epilepsy or it could be on limbs for treating other nervous system impairments, e.g. phantom pains treatment.

In a first aspect the invention provides a stimulation media fixation unit for electrical and/or mechanical stimulation of nerves of a living being, configured to be arranged in a formed channel in and out of the skin, where the stimulation media fixation unit includes at least one electrode and/or at least one vibration generator configured to be placed in close proximity of a portion of a nerve of a living being, including connection/s to a pulse generator configured to provide a sequence of electrical pulses, and/or mechanical vibrations, to the at least one electrode, or vibration generator/s, in order to achieve stimulation of the nerve, where the stimulation media fixation unit has a first end and a second end, where the first end of the stimulation media fixation unit is configured to protrude out of the first end of the formed channel and the second end of the stimulation media fixation unit is configured to protrude out of the second end of the formed channel and where at least one end termination member, configured to be dismantled from and reassembled to the stimulation media fixation unit body, is configured to provide a stop for movement of the stimulation media fixation unit body in at least one direction within the formed channel, where the at least one end termination is positioned outside the first and/or second end of the formed channel, providing a mechanically interlocking mechanism by means of geometry of the end termination for the stimulation media fixation unit and specially adapted for providing tissue fixation enhanced through adhesion to the surrounding tissue where the electrode member is a high-tack hydrogel-based electrode member.

In another embodiment, the invention provides a system for electrical stimulation of nerves of a living being, including a stimulation media fixation unit configured to be arranged in a formed channel in and out of the skin, and specially adapted for providing fixation of at least one hydrogel-based electrode member/s configured to be placed in close proximity of a portion of a nerve of a living being, and a pulse generator configured to provide a sequence of electrical pulses, and/or mechanical vibrations, to the at least one hydrogel-based electrode, or vibration generator, for stimulation of the nerve, where the stimulation media fixation unit has a first end and a second end, where the first end of the stimulation media fixation unit is configured to protrude out of the first end of the formed channel, and the second end of the stimulation media fixation unit is configured to protrude out of the second end of the formed channel, and where the stimulation media fixation unit body member is forming the structure of the stimulation media fixation unit, the stimulation media fixation unit body constituting the fixation member onto which the at least one hydrogel-based electrode and/or vibration generator is arranged or included, and where at least one end termination member, configured to be repeatedly non-destructively dismantled from and reassembled to the stimulation media fixation unit body, is configured to provide a stop for movement of the stimulation media fixation unit body in at least one direction within the formed channel, where the at least one end termination is positioned outside the first and/or second end of the formed channel, providing a mechanically interlocking mechanism by means of geometry of the end termination for the stimulation media fixation unit when the electrode fixation unit is arranged in the formed channel.

In an embodiment, the stimulation media fixation unit, now serving as a vibration generator fixation unit, includes a system for mechanical vibrations stimulation of nerves of a living being, through application of at least one built-in vibration generator providing either linear, rotational, shaking, shivering or inhomogeneous random vibrations and thus mechanically activating the surrounding tissue to trigger nervous response, utilizing embodiments with an internally elongated form and the mechanically interlocking and tissue adhesion to effectively transfer the vibration energy in the form of sinusoidal, linear, rotational, shaking, shivering haptic movements or random vibration of various amplitudes and frequencies to the targeted tissue, when the stimulation media fixation unit is arranged in the formed channel.

In embodiments of the stimulation media fixation unit not including electrode member/s, the stimulation media fixation unit constitutes a vibration generator fixation unit.

In an embodiment, the vibration generator is a trembler configured to provide vibrations in the form of rotational movements.

In another embodiment the vibration generator is configured to provide vibrations in the form of linear movements.

In an embodiment the vibration generator is a haptic linear resonator.

In yet another embodiment, the vibration generator is a piezo-element.

It has to be understood, that the stimulation intensity of the vibration generation is adjustable, within the force range of 0.05 g to 10 g. The mode of action is controlled by frequency and/or amplitude and/or time-span patterns. Some patients prefer the lowest clinically relevant stimulation intensity, where others prefer clearly perceptible levels of stimulation intensity. The clinical performance of the vibration stimulation is depending on the size and/or weight of the stimulation media fixation unit in which the vibration generator is arranged and the site of implantation, where tissue types and distances to the nerves plays the main roles. For daily use, stimulation intervals can be setup allowing for personal patient-controlled adjustment to meet the individual user's stimulation intensity needs throughout the day. For the exemplified application, where the vibration stimulation is directed to the genital nerves, a host response of triggering sexual arousal as a side-effect is possible, although such host response is not the main focus of this invention.

In an embodiment, the system is adapted to simultaneously provide electrically stimulation and mechanical stimulation.

In an embodiment, the at least one end termination member is attached to an end of the stimulation media fixation unit body but with a gap between the end termination member and the other end of the stimulation media fixation unit body featuring or not featuring another end termination member. It has to be understood that fixation to the skin does not rely on forming a completely closed loop but on a maintaining a safe fixation which will also be the case even if there is formed a gap.

In an embodiment, the stimulation media fixation unit is configured to repeatedly be non-destructively dismantled into at least two elements and reassembled, to allow exchange of the at least one hydrogel-based electrode member/s, and repositioned to the stimulation media fixation unit and placed into the initially arranged formed channel, the at least one hydrogel-based electrode member being a monopolar electrode member, bipolar electrode member, or multi-polar electrode member, and where the bipolar or multi-polar electrode member is provided in a single component or in multiple components to be arranged on the stimulation media fixation unit, where the electrical connection to the at least one electrode member is formed internally in the stimulation media fixation unit, thus inside the at least one electrode member.

In an embodiment, the hydrogel member is a hydrogel suitable for electrical stimulation.

In an embodiment, the stimulation media fixation unit functions as a vibration generator fixation unit the hydrogel is a hydrogel not suitable for electrical stimulation.

In an embodiment, the at least one electrode member is having bipolar or multi-polar electrode configurations and constitutes a hydrogel-based electrode member, and the at least second electrode constitute a non-hydrogel-based electrode member made from biocompatible electrical conductible material being one or more of medical grade titanium, medical grade stainless steel, platinum, platinum/iridium, medical grade metals and other precious metal alloys frequently used for electrical stimulation applications, and/or fully or partially surface treated medical grade metals coated using Titanium-nitride, diamond-like carbon etc. for adjustment of e.g. electrode member impedance.

In an embodiment, at least one hydrogel-based electrode member is integrated into the stimulation media fixation unit and constitutes the stimulation media fixation unit body.

In an embodiment, the at least one electrode member is configured with outer surface partially or totally constituting hydrogel as interface for the tissue in the formed channel through the skin, the eventual remaining surface area being either metallic, ceramic or polymeric based.

In one embodiment, the stimulation media fixation unit, in a monopolar configuration, includes at least one electrode member made from non-hydrogel-based materials and comprises means for injecting a non-plasticized hydrogel through the at least one end termination and through the stimulation media fixation unit, which leaks the non-plasticized hydrogel into the formed channel through the tissue, enhancing the electrical performance of the non-hydrogel-based electrode member/s.

In an embodiment of the exchangeable hydrogel-based electrode member or integrated hydrogel-based electrode member, a connecting spring member is forming the electrode inner part and electrical contact to the stimulation media fixation unit outer surface, where a scrim member is enhancing the mechanical integrity of the at least one electrode member, serving as a fixture for the hydrogel element, the hydrogel element itself is assembled and cured into a single unit forming an electrode member.

In an embodiment of the exchangeable hydrogel-based electrode member or integrated hydrogel-based electrode member, an isolating or conductive boundary element is attached to the first and/or second end of the electrode member.

In another embodiment of the exchangeable hydrogel-based electrode member or integrated hydrogel-based electrode member, the body of the electrode member is configured with a solid electrically conducting element, which is forming electrical connection to the stimulation media fixation unit body through means of conductive springs, conductive rubber, fixed parts using screws or similar constructive elements, or click-in feature parts designed into the end terminations of the stimulation media fixation unit. By this way, the conductive boundary element is extending the curve-length of the stimulation media fixation unit and fixed by means of the assembly of the at least one end termination to the stimulation media fixation unit.

As the hydrogel-based electrode members arranged on the stimulation media fixation unit is adhering to the tissue or highly frictional, a tool is provided for the insertion of the stimulation media fixation unit body into the formed channel through the skin. Lubrication of the at least one electrode member/s by e.g. use of water or saline could be usable, but such means postpones the adhesive function of the hydrogel-based electrode members until the water or saline is sufficiently dried out and is therefore a less attractive method.

For the purpose of inserting the stimulation media fixation unit through the skin in the formed channel, at least one end termination shall be capable of being nondestructively removed, and reassembled onto the stimulation media fixation unit, once the stimulation media fixation unit is arranged in the intended position in the formed channel through the skin. Another end termination unit is arranged in the second end of the stimulation media fixation unit, which includes an electrical connector, interfacing to a pulse generator, or to a lead connected to a pulse generator, the pulse generator capable of providing electrical stimulation charge and/or power-signals suitable for vibrations stimulation.

In one embodiment of the insertion tool for a stimulation media fixation unit including at least one hydrogel-based member and with one removeable end termination removed, the insertion tool includes a polymer or silicone-based needle with a polymer or silicone-based tubing attached, into which the stimulation media fixation unit is arranged and covered with two layers of said polymer or silicone-based tubing, in such a way, that the polymer or silicone-based tubing is peeled off the stimulation media fixation unit when being positioned in the formed channel through the skin.

In another embodiment of the tool for insertion of stimulation media fixation units, the insertion tool has a tip that includes a metal or ceramic-based needle for guiding the insertion including the stimulation media fixation unit through a formed channel through the skin.

In an embodiment of the insertion tool, the insertion tool tip is blunt.

In an embodiment of the insertion tool, the insertion tool tip is sharp.

In an embodiment of the insertion tool, the insertion tool is partially or entirely coated with a low friction silicone primer.

In an embodiment of the insertion tool, the insertion tool is partially or entirely coated with a conformal coating such as poly paraxylylene coating.

In an embodiment of the insertion tool, the insertion tool tip is solid-, hollow- or tubular-formed and the cross section is having a triangular, squared or multiple angled cross section until substantially being circular or elliptical formed with even or uneven sized sides and/or with straight or curved sides and where the stimulation media fixation unit in the longitudinal direction can travel in a straight or bended or curved or spiral or meandering or a combination of said travel form directions, and the shape of the insertion tool tip varies with straight or shaped tool tip bodies of various designs and sizes.

In an embodiment, the stimulation media fixation unit body is solid-, hollow- or tubular-formed and the cross section is having a triangular, squared or multiple angled cross section until substantially being circular or elliptical formed with even or uneven sized sides and/or with straight or curved sides and where the stimulation media fixation unit in the longitudinal direction can travel in a straight or bended or curved or spiral or meandering or a combination of said travel form directions.

In embodiments of the invention, the shape of the stimulation media fixation unit varies with straight or shaped stimulation media fixation unit bodies of various designs and sizes.

In an embodiment, the stimulation media fixation units is configured to the preference and needs of the individual user having cross sections ranging from a diameter of one millimeter to ten millimeters with a typical stimulation media fixation unit body length in the range of ten to forty millimeters. The curvature of the stimulation media fixation unit can vary relative to the tissue variation or personal preferences from straight to complete enclosed designs and the said curvature need not be constant.

In embodiments, the stimulation media fixation unit comprises a biocompatible electrical conductible material such as medical grade titanium, medical grade stainless steel, platinum, platinum/iridium, medical grade metals and other precious metal alloys suitable for electrical stimulation and/or comprises a biocompatible electrical isolating material such as silicone, polyurethane, ceramics, PTFE or PEEK and/or comprises a flexible or resilient material.

In embodiments, the stimulation media fixation unit includes hydrogels formulated to meet specific application requirements, biocompatible thermoplastic materials such as Polyether-ketone based materials, HD-PE, PP, PET, Fluorinated polymer materials, or other sterilizable materials suitable for permanent contact through the skin of the patient.

In an embodiment, the stimulation media fixation unit is made from surgical steel like 316 LVM, titanium-based alloys and precious metal alloys.

In an embodiment, the stimulation media fixation unit is made from ceramics. Ceramics may be used for shorter lengths and/or larger dimensions of the stimulation media fixation unit body.

In an embodiment, the at least one of the first or second ends of said stimulation media fixation unit body are configured with a part which forms a stop for moving the stimulation media fixation unit through the formed channel in the tissue in one direction. When the system is not activated the lead providing the stimulating signal can be removed entirely to allow the user to have maximum freedom from relevant inconveniences.

When initially inserted into the tissue, the end terminations of the stimulation media fixation unit form a stable fixation mechanism for having a fixed position specifying a fixed distance to the nerve of interest. Thus, the stimulation media fixation unit serves as a stable platform for arranging one or more electrodes for submitting a neuromodulation signal addressed to the nerve of interest. For securing the stimulation media fixation unit in the fixed position in the formed channel, at least one end termination on the stimulation media fixation unit is provided to avoid that the stimulation media fixation unit can move out of the formed channel in the tissue. When inserted into the formed channel through the skin, an end termination can be provided in the end not initially being equipped with an end termination. The end termination can be provided in various ways.

It has to be understood that the end termination can be formed in various ways almost without any limits. However, considerations to the design need to address risks of infections if such would result in end termination designs that are difficult to maintain hygienically. Too pointy shapes and overly detailed objects may thus not be suitable as end termination, given the exemplified location at the genitals.

In an embodiment, the end termination is formed by configuring the end of the stimulation media fixation unit at least on a part of the first or the second end that is configured to protrude out of the formed channel with a cross-section that is larger than the measured circumscribed cross-section of the formed channel in such a way as to form a stop for movement of the stimulation media fixation unit through the formed channel in one direction.

In an embodiment, the end termination is formed by configuring the end of the stimulation media fixation unit at least on a part of the first or the second end that is configured to protrude out of the formed channel with a thread for receiving a nut, said nut having a cross-section that is sufficiently larger than the measured cross-section of the formed channel in such a way as to form a stop for movement of the stimulation media fixation unit through the formed channel in one direction.

In an embodiment, the stop is provided by adding an end termination by snapping it onto the stimulation media fixation unit body. For the insertion and since the electrode member/s may need to be exchanged, it shall be possible to remove the end termination to allow an easy way to remove the stimulation media fixation unit out of the tissue, without clinical intervention. The attachment of the end termination can include click-in features involving a spring member, or a magnet member, thread or similar interface between the stimulation media fixation unit body and the end termination.

The end terminations to be arranged on the stimulation media fixation unit body ends can be designed in various ways, where one or all end terminations can be exchanged or interchanged to the preference of the wearer, to match for instances the skin or tissue color, or to match the size of the end termination to the taste of the user.

In an embodiment, the stimulation media fixation unit is designed to have two exchangeable end terminations of various designs for the preference of the wearer. The stimulation media fixation unit has two corresponding features of various designs to allow attachment of the electrode member/s into or onto the stimulation media fixation unit.

In an embodiment, the end terminations are threaded internally or have an external thread, which allows exchange of electrode member/s or stimulation media fixation units. Other forms of attachment include click-in features involving a spring feature, or a magnet interface between the stimulation media fixation unit body and the end termination.

In an embodiment, an end of the stimulation media fixation unit, at least on a part of the first and/or the second end that is configured to protrude out of the formed channel is configured with an interface for receiving a detachable end termination, the end termination being attached and secured in position by means of spring-loaded or magnetic force or click-in or by a threaded connection.

In more sophisticated embodiments, the stimulation media fixation unit is partly made of an electrical isolating material and having electrical conductible sections which serve as suitable electrode member/s. In an embodiment, the electrode member/s are each forming independent electrodes supplied by different nerve stimulation signals or supplied from the same electrical stimulation pattern source or serving as anodes and cathodes.

In an embodiment, the stimulation media fixation unit body is hollow and the electrical connection/s to the electrode/s are running inside the stimulation media fixation unit body and is terminated in a connector accessible from outside the stimulation media fixation unit. A monopolar electrode device can be provided in this way but also bipolar or multipolar electrode devices.

In an embodiment, the stimulation media fixation unit, with or without attached end terminations, forms an electrical isolating part where the at least one electrode or multiple electrodes are arranged on or in the stimulation media fixation unit in a position where the stimulation media fixation unit is adapted to be in contact with the tissue inside the formed channel through skin.

In an embodiment, the at least one end termination comprises electrically isolating materials, such as PEEK, fluorinated materials, ceramics or similar nonconductive materials.

In an embodiment, the at least one end termination constitutes an electrical stimulating electrode utilizing conductive materials constituting an electrode member.

In an embodiment, the stimulation media fixation unit comprises at least one detachable electrical connection providing the stimulation signal from a pulse generator to the at least one applied electrode.

In an embodiment, the system comprises an electrical connection between the electrode arranged on the stimulation media fixation unit and the pulse generator.

In an embodiment of the invention, the pulse generator is arranged in, on or with the stimulation media fixation unit.

In an embodiment, the pulse generator is connected to the stimulation media fixation unit via a detachable leaded connection. The pulse generator is in an embodiment arranged remotely from the stimulation media fixation unit.

In an embodiment, the system comprises a leaded electrical connection between the at least one electrode and the pulse generator and comprises further a connector configured for releasing the leaded electrical connection to the pulse generator when a preconfigured pull force is exceeded. The connection can be reobtained simply by re-connecting the leaded connection to the stimulation media fixation unit. The socket is in an embodiment a plug and socket connector. This is an appreciated behavior since pulling the stimulation media fixation unit when in place in the tissue can be harmful or painful to the user. Thus, a safety arrangement as explained will simply decouple the lead and protect the user from harm at a designed level of forces.

In an embodiment, the electrode is supported in situ in a spring retained arrangement in such a way that when a preconfigured pull force is exceeded on the leaded connection, the electrode and/or the lead is released from its position on the stimulation media fixation unit or the patch member. This is another solution for protecting the user against pulling the stimulation media fixation unit in the formed channel.

It has to be understood that electrical stimulation will need a signal to be provided through a first electrode, which will return to the pulse generator via a second connection or electrode. Thus, the invention also comprises a second electrode that in embodiments are arranged on the stimulation media fixation unit, or with the pulse generator serving as a counter electrode for the at least one electrode arranged on the stimulation media fixation unit.

Electrode dislocation, in relation to the nerve of interest, has fatal consequences for the efficacy of the system. The establishment of a stable nerve electrode interface is of crucial importance for systems applying electrical stimulation of nerves in order to treat physical disorders.

BRIEF DESCRIPTION OF THE DRAWINGS

For the purpose of illustrating the invention, forms are shown in accompanying drawing, which are presently preferred, it being understood that the invention is not intended to be limited to the precise arrangements and instrumentalities shown. The invention includes.

DETAILED DESCRIPTION

Figure 1:
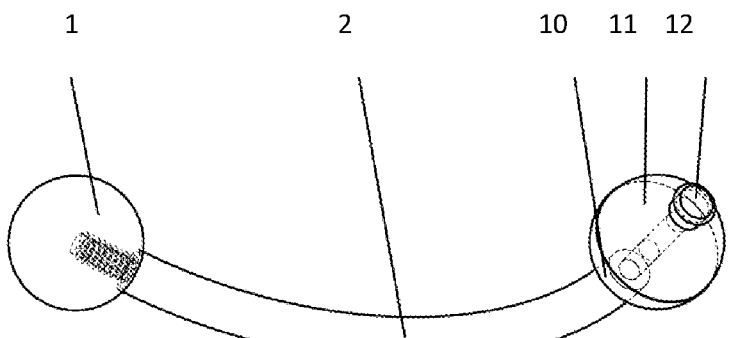
FIG. 1, illustrates a smoothly bended embodiment of the stimulation media fixation unit body (2) configured for addition of a hydrogel-based electrode member, with one end termination (1) attached using threads and one end termination magnetically attached (10), the latter end termination allowing for electrical connection (11, 12) via a connector and lead to a pulse generator.

FIG. 1 represents a stimulation media fixation unit body (2), where the method of end termination (1) attachment is shown using threads. The stimulation media fixation unit body (2) can be solid as well as hollow and forms the fixation member for the hydrogel-based electrode element to be arranged on the stimulation media fixation unit. The end terminations and the stimulation media fixation unit body could as well be assembled using clicked-in, magnetically attached, spring loaded or attached using similar concepts. The shape or design of the end terminations is preferably round and ball-shaped to be the least sharp as possible, and to allow easy hygienically maintenance and thus avoid infectious circumstances. Other designs are optional as long as they are hygienically acceptable and does not harm the surrounding tissue. The end termination providing connection (12) to a lead or a pulse generator is electrically isolated from the skin (10). A second end termination element (11) provides a magnetically counterpart of the electrical connection (12) and may be conductive or non-conductive.

The isolating materials of the end termination/s (10 and/or 11), when designed not to be part of the electrode interface, can comprise PEEK, fluorinated materials, ceramics or similar biocompatible materials. When the lower section (10) of the end termination shall be part of the electrode interface, this part is then design utilizing 316L or precious metals suitable for the application. Thus, the stimulation media fixation unit body and/or the at least one end termination constitutes an electrical stimulating electrode.

The shape of the stimulation media fixation unit can vary, having the goal to position the hydrogel-based electrode/s and/or other suitable conductive electrode/s arranged on the stimulation media fixation unit or being an integral part/s of the stimulation media fixation unit, close to the targeted nervous tissue for optimal stimulation effectivity. Further, the level of tissue adhesion enhances the performance of the electrode/tissue interface.

Therefore, the bending radii and bending angles shall be configured or selected in accordance with the specific site of interest. The preferred cross sections of the stimulation media fixation unit body are ranging from ø1 mm to 06 mm, although not necessarily being circular. Sections of the stimulation media fixation unit body having larger circumference, i.e. up to 10 mm, could be optional where a large charge injection is important for the application. The preferred shaft lengths are from 10 mm to 40 mm and should be anatomically feasible for the site at which the stimulation media fixation unit is intended to function. The length of the stimulation media fixation unit body can be more than 100 mm, but if longer distances of fixation are necessary, application of additional stimulation media fixation units is preferred. The curvature of the stimulation media fixation unit determines the depth of the stimulation media fixation unit into the tissue. The requirement for this depth can vary depending on the local tissue at the site of stimulation, taking into account among other things the length of the stimulation media fixation unit body, the cross section etc., and the anatomical location of stimulation. If the stimulation media fixation unit is too small, the quality of the fixation will drop, with subsequent increased risk of compromised electrode/tissue interface e.g. loss of performance or function.

Figure 2:
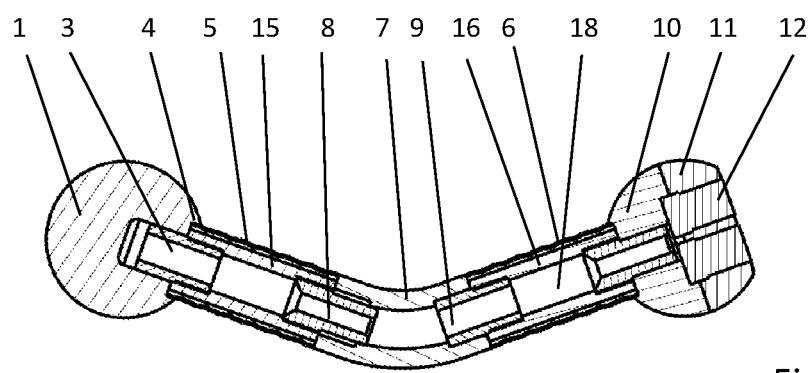
FIG. 2, illustrates a stimulation media fixation unit with integrated hydrogel-based electrode members (5, 6) and with one end termination having integrated connection details (11, 12), configured for optional changes of an electrode member (5 and 15 and/or 6 and 16)

FIG. 2 represents a stimulation media fixation unit with integrated hydrogel electrodes (5, 6) in a bipolar configuration. Tri-polar, quadrupolar or 5-polar electrode concepts could also prove to be relevant options in some applications, although these designs are not included in the illustrations. The shapes of the hydrogel electrode areas (5, 6) are of limited importance but should be smooth enough to allow insertion and prevent sharp edges that may become irritant or even unsafe in the formed channel in the tissue. The electrode areas (5, 6) shall be balanced with the load of charge to be injected, the electrode material chosen, and frequency of use of the application applied. A feature for electrical contact is shown as a magnetic connection (11, 12), but other designs are also relevant, utilizing, spring loads or click-in etc.

The shape of the stimulation media fixation unit body can vary in order to allow the hydrogel-based electrodes (5, 6) to be positioned in close contact with the tissue targeted for the charge injection. The depth of the stimulation media fixation unit into the tissue is ideally between 2 and 5 mm, but further depth, may be required in some cases, where the excitable tissue is found further profound. For this reason, the bending sections (7) should be configured to position the hydrogel-based electrode members (5, 6) at the site of interest. The clinical success of electrical stimulation-based systems depends among other things on the ability of the electrode member/s (5, 6) to consistently provide safe levels of stimulation to the target component of the nervous system. Exceeding the limit for safe charge injection may cause electrode degradation and/or irreversible tissue damage resulting in loss of clinical efficacy and the electrode member (5, 6) degrading and becoming unsafe. To mitigate the problems associated with reduced physical size, advanced biomaterials and precious materials should be used to ensure longevity. The electrode members (5, 6) are the electrochemically active areas of the stimulation media fixation unit where charge transfer occurs during stimulation. The electrode member/s is supposed to be in close proximity of the target nerve to obtain low stimulation thresholds. Ideally, the electrode member/s should have good chemical stability, high charge injection capacity, low electrical impedance, and should remain inserted in the tissue as a compliant material causing low degree of inflammation. Electrical connection (11, 12) to the electrode member/s (5, 6), run inside the stimulation media fixation unit body members (7, 8, 9, 16, 10).

The internal wiring can also be obtained by the structural parts of the electrodes themselves, or by partially coating of for instance a ceramic based stimulation media fixation unit body. In this manner, simplification of assembly of the stimulation media fixation unit is obtained. For the positioning of the stimulation media fixation unit, at least one end termination (1) shall be detachable, or a separable stimulation media fixation unit body should be used, as presented in FIG. 2.

Figure 3:
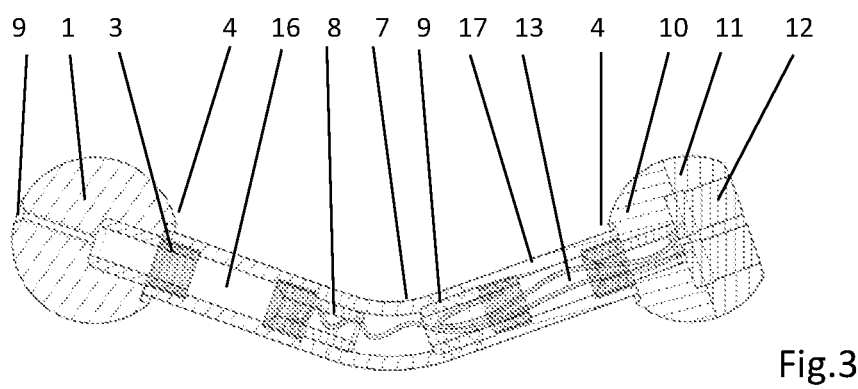
FIG. 3, illustrates a stimulation media fixation unit configured for addition of the in FIG. 5 illustrated hydrogel electrode member, or singular hydrogel electrode member/s and isolator member/s if required for e.g. bipolar stimulation media fixation unit configurations.
Figure 5:
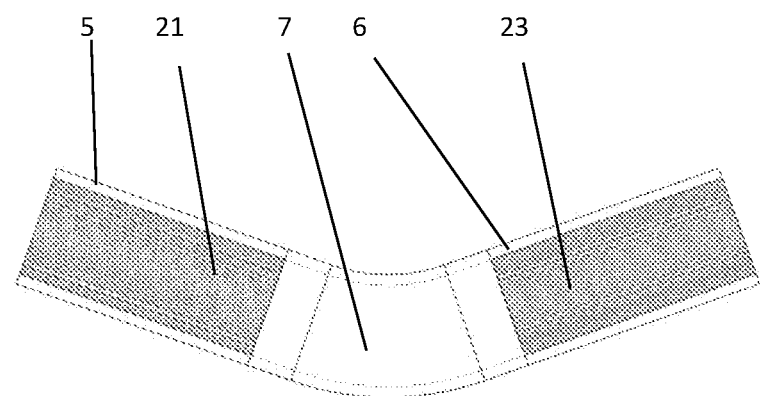
FIG. 5, illustrates a hollow hydrogel-based electrode member (5, 6) to be arranged on the described stimulation media fixation unit of FIG. 3 or that of FIG. 4, where a flexible electrode member (5, 6) is positioned in the first end and second end of the isolation member (14)

FIG. 3 illustrates stimulation media fixation unit configured for addition and/or exchange of hydrogel-based electrode member/s, as e.g. presented in FIG. 5, where the stimulation media fixation unit of FIG. 3 includes an end termination (1) having a channel (9) for injection of liquids to support the removal of the stimulation media fixation unit. Thus, the thread element (3) shall also include an open pathway for liquid to flow through it. Holes are prepared in the isolation member (7), leaking the liquid into the channel in the tissue, reaching the hydrogel-based electrode member/s (5, 6) lubricating the hydrogel for ease of removal. In monopolar configurations of the stimulation media fixation unit, the liquid could be a non-plasticized hydrogel, supporting electrical performance of the hydrogel-based electrode.

The end terminations (1, 10) further have a detail (4), ensuring the correct positioning and fixation of the electrode member to be included and additionally limiting edge biting effects from the edge/s of the electrode member/s.

The stimulation media fixation unit body members (16, 8, 7, 9, 17 and 13) provide the charge pathway to the electrode member/s (5, 21 and/or 6, 23) illustrated in FIG. 5. The stimulation media fixation unit body member/s (16, 17) includes a contact surface for the hydrogel-based electrode member/s inner structure. This contact surface can include a spring connection to improve the connection from the stimulation media fixation unit body member/s (16, 17) to the electrode member inner structure (21, 23). The physical size of the first stimulation media fixation unit body member (16) should not necessarily be identical to that of the second stimulation media fixation unit body member (17), but the size of the stimulation media fixation unit body member/s shall match that of the hydrogel-based electrode member/s to be attached to the stimulation media fixation unit body.

Figure 4:
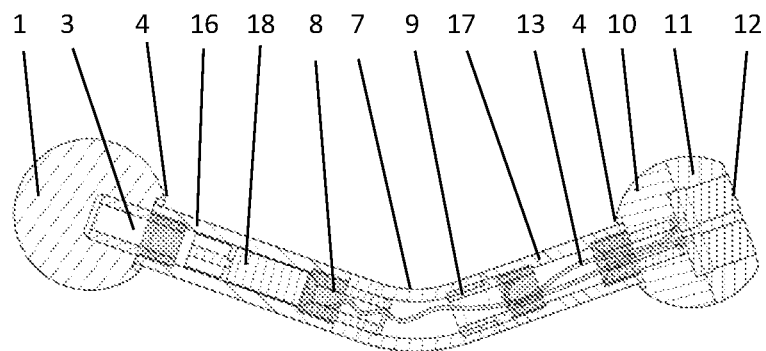
FIG. 4, illustrates a stimulation media fixation unit including a vibration generator (18) configured for addition of the in FIG. 5 illustrated hydrogel electrode member, or singular hydrogel electrode member/s and isolator member if required for e.g. bipolar stimulation media fixation unit configurations.

FIG. 4, illustrates a stimulation fixation unit body, which includes a vibrations generator micromotor (18), positioned inside an electrode member (16). Due to the presence of the micromotor for vibration stimulation, a pathway as included in FIG. 3 is not optional. Apart from this detail, the designs of FIG. 3 and FIG. 4 are identical.

FIG. 5, illustrates a hollow hydrogel-based electrode unit to be arranged on the above described stimulation media fixation unit body of FIG. 3 or FIG. 4, where a flexible electrode member (5, 6) is positioned in the first end and second end of the isolation member (7). It should have a smooth surface and overall structure also at the transition/s between the hydrogel-based electrode member/s and the isolation member (7), to prevent risk of harm inside the formed channel in the tissue, even though the hydrogel (5, 6) is considered a soft and flexible material. The isolating material of the isolation member (7), if any applied in the given design, should be biocompatible or bio-inert, of which PEEK or ceramics are ideal. Other materials could include fluorinated based materials.

The internal structure (21, 23) of the electrode unit of FIG. 5, is an electrically conductive spring member, providing contact pressure forces to the stimulation media fixation unit body it shall be attached to. This can be achieved in various ways, by e.g. making the internal structure (21, 23) slightly nonconforming to the stimulation media fixation unit body it should be attached to, exemplified as a slightly triangularly internal structure (21, 23) fitted for a circular stimulation media fixation unit body.

Other way to create the required contact pressure is by use of an internal structure (21, 23), having a radially spring force such as the commercially available Bal-Seal engineering canted coil springs, or slightly undersized precision coil springs fitted to a matched size of stimulation media fixation unit body.

The inner structure can also include a scrim or mesh to improve the attachment of the hydrogel member (5, 6) to the inner structure member (21, 23) of the electrode.

Figure 6:
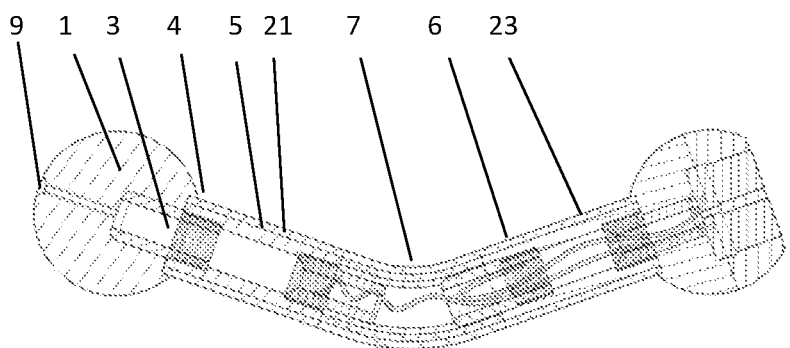
FIG. 6, illustrates a complete stimulation media fixation unit including a stimulation media fixation unit as described in FIG. 3 or FIG. 4, with the electrode unit member as described in FIG. 5 positioned onto the stimulation media fixation unit body, forming a ready for use stimulation media fixation unit.

FIG. 6, illustrates a complete stimulation media fixation unit body as described in FIG. 3 and FIG. 4, with the electrode member as described in FIG. 5 positioned onto the stimulation media fixation unit body, forming a ready for use stimulation media fixation unit. For designs where the stimulation media fixation unit body is heavily bended, i.e. the angles between the first end and the second end of the isolation member (7) constitutes a circular section of more than 15°, the isolation member (7) shall be able to flexibly adopt this bending degree. Likewise, the hydrogel electrode member (5 and 21 or 5 and 23) shall allow bending similarly.

Figure 7:
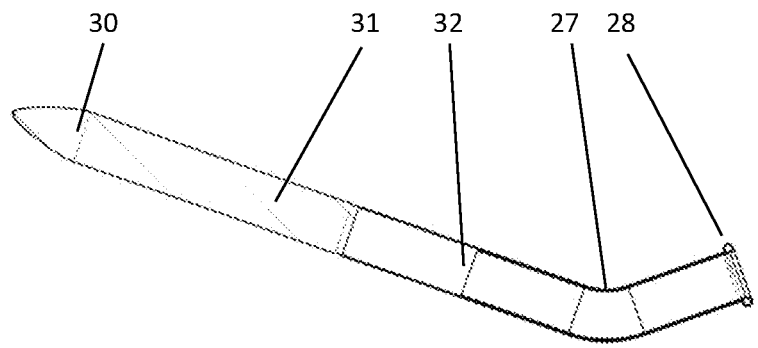
FIG. 7, illustrates an insertion tool configured for any of the above described stimulation media fixation units.

FIG. 7, illustrates an insertion tool configured for any of the above described stimulation media fixation units. The tip (30) is in some embodiments blunt, used for insertion of stimulation media fixation units into established and healed channels through the skin. The tip (30) is in some embodiments sharp, for initial creation or re-creation of the channel through the skin and is established from polymers, metal and/or ceramics. Both embodiments include variants where these are coated with a low friction silicone primer.

The insertion tool presented in FIG. 7 includes a polymer or silicone-based needle-shaft (31) for guiding the stimulation media fixation unit through the formed channel through the skin and a polymer or silicone-based tubing (27) into which the stimulation media fixation unit shall be arranged. The diameter, length and shape shall be matched to the stimulation media fixation unit to be positioned in the formed channel.

Figure 8:
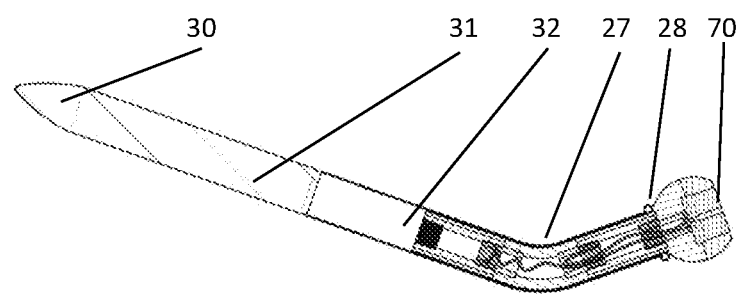
FIG. 8, illustrates an insertion tool including any of the previous described embodiments of stimulation media fixation units, arranged inside the insertion tool is such a way that the polymer tubing (27) can be rolled of inside the formed channel through the skin.

FIG. 8 illustrates an insertion tool (30, 31, 32, 27 and 28) including any of the previous described embodiments of stimulation media fixation units (70), arranged inside the insertion tool is such a way that a polymer tubing (27) can be peeled and rolled off the stimulation media fixation unit (70) inside the formed channel through the skin, in such a way, that the polymer tubing (27) is peeled off the stimulation media fixation unit (70). The stimulation media fixation unit (70) have the first end termination removed, then positioned at the polymer tubing end (32) and rolled onto the stimulation media fixation unit, forming a neck (28) at the second end termination on the stimulation media fixation unit (70). This procedure covers the stimulation media fixation unit (70) in two layers of polymer tube (27). This provides additionally a means of protection of the hydrogel electrode member/s (5, 6) for increase of shelf life.

The polymer tube (27) is the preferred embodiment made from elastic materials, of which silicone is preferred. Similar tubing could be made from polyurethane with low wall thickness, or other materials with at least similarly low durometers.

Figure 9:
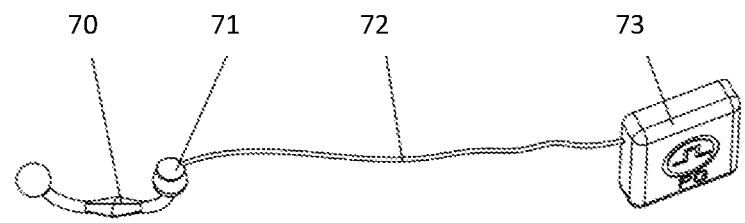
FIG. 9, illustrates an example of the entire system, where the stimulation media fixation unit (70) may be any of the above described stimulation media fixation units, and where the connector (71) of a lead (72) is positioned on the stimulation media fixation unit connector end termination and connected to a pulse generator (73).

FIG. 9 shows an example of an entire electrical stimulation system, represented by a stimulation media fixation unit (70), where the lead (72) is detachable and is designed to release connection (71) at a predetermined force, the preferred method of connection being magnetically support. A similar connection can be arranged on the pulse generator (73). The lead shall hold at least the corresponding number of wires as the stimulation media fixation unit holds electrodes, and if also equipped with a vibration generator additional wires for powering said vibration generator, and hence any of the previous systems illustrated in FIG. 1 to FIG. 6 could constitute the stimulation media fixation unit (70) as shown in FIG. 9.

The invention claimed is:

1. A system for stimulation of a nerve of a living being, including a stimulation media fixation unit including a body member, a hydrogel-based electrode member, and at least one end termination member, the stimulation media fixation unit configured to be arranged in a formed channel in and out of the skin of the being, and adapted for providing fixation of the hydrogel-based electrode member configured to be placed in close proximity of a portion of the nerve of the living being, and a pulse generator configured to stimulate the nerve of the living being by providing a sequence of electrical pulses to the hydrogel-based electrode, for stimulation of the nerve, where the stimulation media fixation unit has a first end and a second end, where the first end of the stimulation media fixation unit is configured to protrude out of a first end of the formed channel, and the second end of the stimulation media fixation unit is configured to protrude out of a second end of the formed channel, and where the body member of the stimulation media fixation unit forms the structure of the stimulation media fixation unit, the stimulation media fixation unit body member constituting a fixation member onto which the hydrogel-based electrode is arranged or included, and where the at least one end termination member is configured to be repeatedly non-destructively dismantled from and reassembled to the stimulation media fixation unit body member and is configured to provide a stop for movement of the stimulation media fixation unit body in at least one direction within the formed channel, where the at least one end termination is positioned outside the first and/or second end of the formed channel, providing a mechanically interlocking mechanism by means of geometry of the end termination for the stimulation media fixation unit when the electrode fixation unit is arranged in the formed channel.

2. The system according to claim 1, wherein the system is adapted to simultaneously provide electrical stimulation and mechanical stimulation.

3. The system according to claim 1, wherein the at least one end termination member is attached to an end of the stimulation media fixation unit body member but with a gap between the end termination member and the other end of the stimulation media fixation unit body member featuring or not featuring another end termination member.

4. The system according to claim 1, wherein the stimulation media fixation unit is configured to repeatedly be non-destructively dismantled into at least two elements and reassembled, to allow exchange of the at least one hydrogel-based electrode member/s, and repositioned to the stimulation media fixation unit and placed into the initially arranged formed channel, the at least one hydrogel-based electrode member being a monopolar electrode member, bipolar electrode member, or multi-polar electrode member, and where the bipolar or multi-polar electrode member is provided in a single component or in multiple components to be arranged on the stimulation media fixation unit, where an electrical connection to the at least one electrode member is formed internally in the stimulation media fixation unit, thus inside the at least one electrode member.

5. The system according to claim 1, wherein the at least one electrode member has bipolar or multi-polar electrode configurations and constitutes a hydrogel-based electrode member, and an at least second electrode constitutes a non-hydrogel-based electrode member made from biocompatible electrical conductible material being one or more of medical grade titanium, medical grade stainless steel, platinum, platinum/iridium, medical grade metals and other precious metal alloys, and/or fully or partially surface treated medical grade metals coated for adjustment of electrode member impedance.

6. The system according to claim 1, wherein the at least one electrode member is configured with an outer surface partially or totally constituting hydrogel as an interface for the tissue in the formed channel through the skin, the eventual remaining surface area being either metallic, ceramic or polymeric based.

7. The system according to claim 1, wherein the system comprises a connecting spring member and a scrim member, the connecting spring member forms the electrode inner part and electrical contact to the stimulation media fixation unit outer surface of an exchangeable hydrogel-based electrode member or an integrated hydrogel-based electrode member, and where the scrim member enhances the mechanical integrity of the at least one electrode member, serving as a fixture for the hydrogel element, the hydrogel element itself being assembled and cured into a single unit forming the hydrogel-based electrode member.

8. The system according to claim 1, wherein the stimulation media fixation unit has a cross section comprising a diameter of one millimeter to ten millimeters and a stimulation media fixation unit body length in the range of ten to forty millimeters.

9. The system according to claim 1, wherein the end termination is formed by configuring the end of the stimulation media fixation unit at least on a part of the first or the second end that is configured to protrude out of the formed channel with a cross-section that is larger than the measured circumscribed cross-section of the formed channel in such a way as to form a stop for movement of the stimulation media fixation unit through the formed channel in one direction.

10. The system according to claim 1, wherein the end termination is formed by configuring the end of the stimulation media fixation unit at least on a part of the first or the second end that is configured to protrude out of the formed channel with a thread for receiving a nut, said nut having a cross-section that is sufficiently larger than the measured cross-section of the formed channel in such a way as to form a stop for movement of the stimulation media fixation unit through the formed channel in one direction.

11. The system according to claim 1, wherein the stimulation media fixation unit body comprises a connector, the stimulation media fixation unit body is hollow and the hydrogel-based electrode runs inside the stimulation media fixation unit body and is/are terminated in a connector accessible from outside the stimulation media fixation unit.

12. The system according to claim 1, wherein the stimulation media fixation unit comprises at least one detachable electrical connection providing the stimulation signal from a pulse generator to the at least one applied electrode.

13. The system according to claim 1, wherein the pulse generator is arranged in, on or with the stimulation media fixation unit.

* * * * *